United States Patent [19]

Taylor

[11] 4,371,623
[45] Feb. 1, 1983

[54] SOLAR STILL

[75] Inventor: G. Brandt Taylor, Berlin, Mass.

[73] Assignee: William N. Durkin, Boston, Mass.; a part interest

[21] Appl. No.: 233,031

[22] Filed: Feb. 9, 1981

[51] Int. Cl.³ .................. C07C 29/80; C12M 1/38; C12P 7/14
[52] U.S. Cl. ......................... 435/290; 435/3; 435/162; 435/289; 435/316; 435/813; 126/438; 126/450; 126/901; 202/83; 202/154; 202/160; 202/177; 202/180; 202/235; 203/2; 203/19; 203/22; 203/81; 203/100; 203/DIG. 1; 203/DIG. 13; 203/DIG. 16
[58] Field of Search .......... 203/DIG. 1, 22, DIG. 13, 203/DIG. 16, 19, 100, 2; 202/180, 234, 160, 177, 154, 198, 233, 235, 83; 126/450, 438, 901; 435/161, 162, 289, 290, 813, 3, 315, 316; 260/42, 29.1 R; 426/494, 231

[56] References Cited

U.S. PATENT DOCUMENTS

| | | | |
|---|---|---|---|
| 102,633 | 5/1870 | Wheeler et al. | 203/DIG. 13 |
| 1,104,948 | 7/1914 | Woolner | 426/494 |
| 1,302,363 | 4/1919 | Graham | 202/233 |
| 1,548,824 | 8/1925 | Condict | 202/198 |
| 2,080,167 | 5/1937 | Da Valle | 203/22 |
| 2,141,330 | 12/1938 | Abbot | 202/180 |
| 2,247,830 | 7/1941 | Abbot | 126/271 |
| 2,490,659 | 12/1949 | Snyder | 202/205 |
| 2,868,645 | 1/1959 | Neureuther | 426/494 |
| 2,975,107 | 3/1961 | Friedman | 202/52 |
| 3,201,328 | 8/1965 | Williams | 435/290 |
| 3,394,054 | 7/1968 | Hoham | 202/234 |
| 3,810,777 | 5/1974 | Boebel et al. | 126/901 |
| 3,926,738 | 12/1975 | Wilson | 435/290 |
| 4,003,069 | 1/1977 | Hilgers | 354/299 |
| 4,011,190 | 3/1977 | Telkes | 126/901 X |
| 4,019,495 | 4/1977 | Frazier et al. | 126/420 |
| 4,191,166 | 3/1980 | Saarem et al. | 126/420 |
| 4,244,352 | 1/1981 | Foster | 126/418 |
| 4,261,329 | 4/1981 | Walsh et al. | 126/450 |

FOREIGN PATENT DOCUMENTS

| | | | |
|---|---|---|---|
| 2558767 | 7/1977 | Fed. Rep. of Germany | 126/438 |
| 2656490 | 2/1978 | Fed. Rep. of Germany | 126/901 |
| 55-92843 | 7/1980 | Japan | 126/901 |

OTHER PUBLICATIONS

Carley, L. W.: *How to Make Your Own Alcohol Fuels;* Aug. 1980, pp. 62–109.

*Primary Examiner*—Wilbur L. Bascomb, Jr.
*Attorney, Agent, or Firm*—Blodgett & Blodgett

[57] ABSTRACT

Apparatus for preparation and distillation of low-alcohol-content, fermentation products into high-alcohol-content, fuel-grade product using solar energy to carry out the fermentation and distillation. The apparatus includes a solar collector with reflectors, fermenting tanks, a distillation column, and temperature controls. The working fluid for the solar collector is isolated from the fluid being distilled.

11 Claims, 16 Drawing Figures

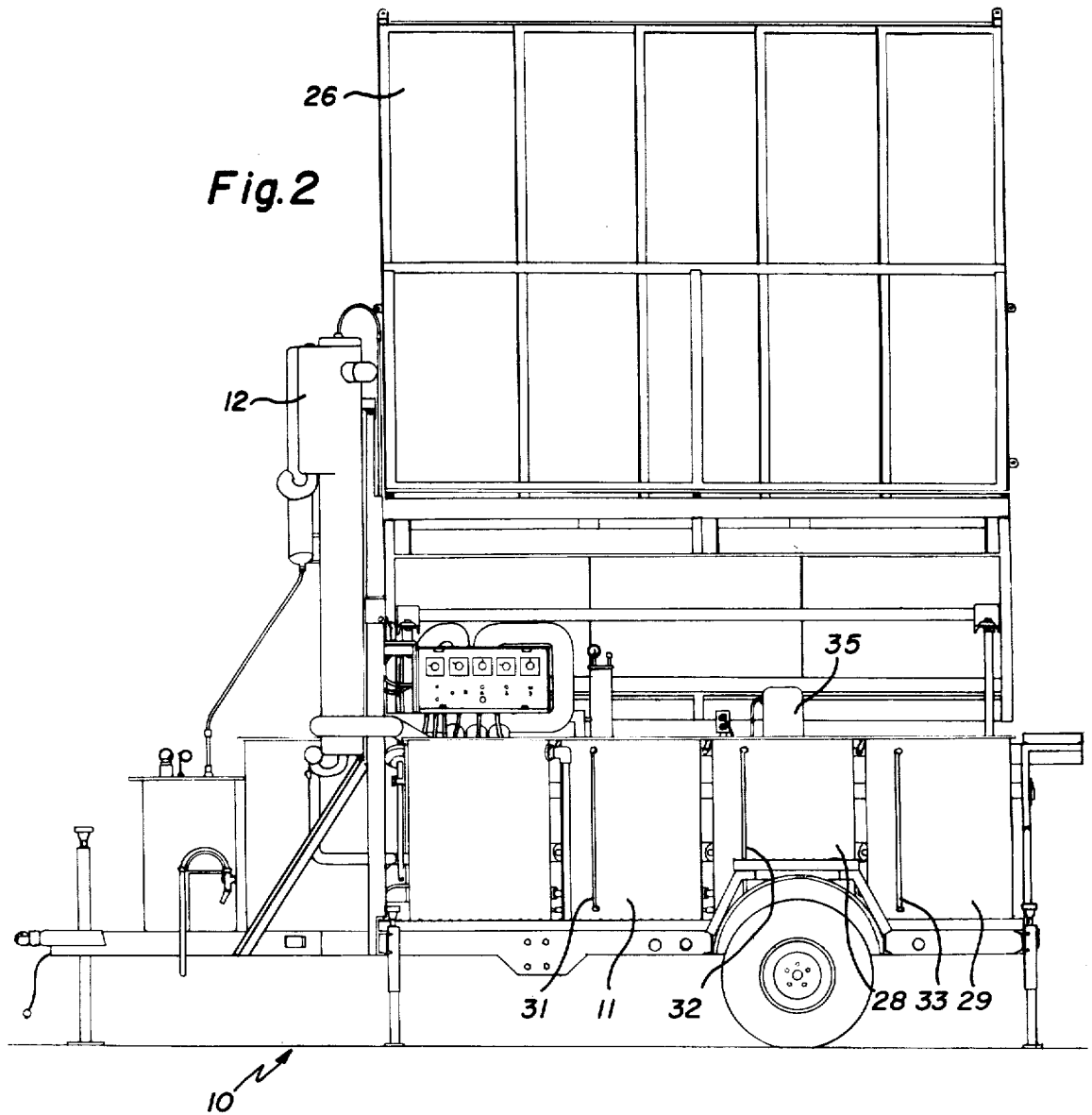

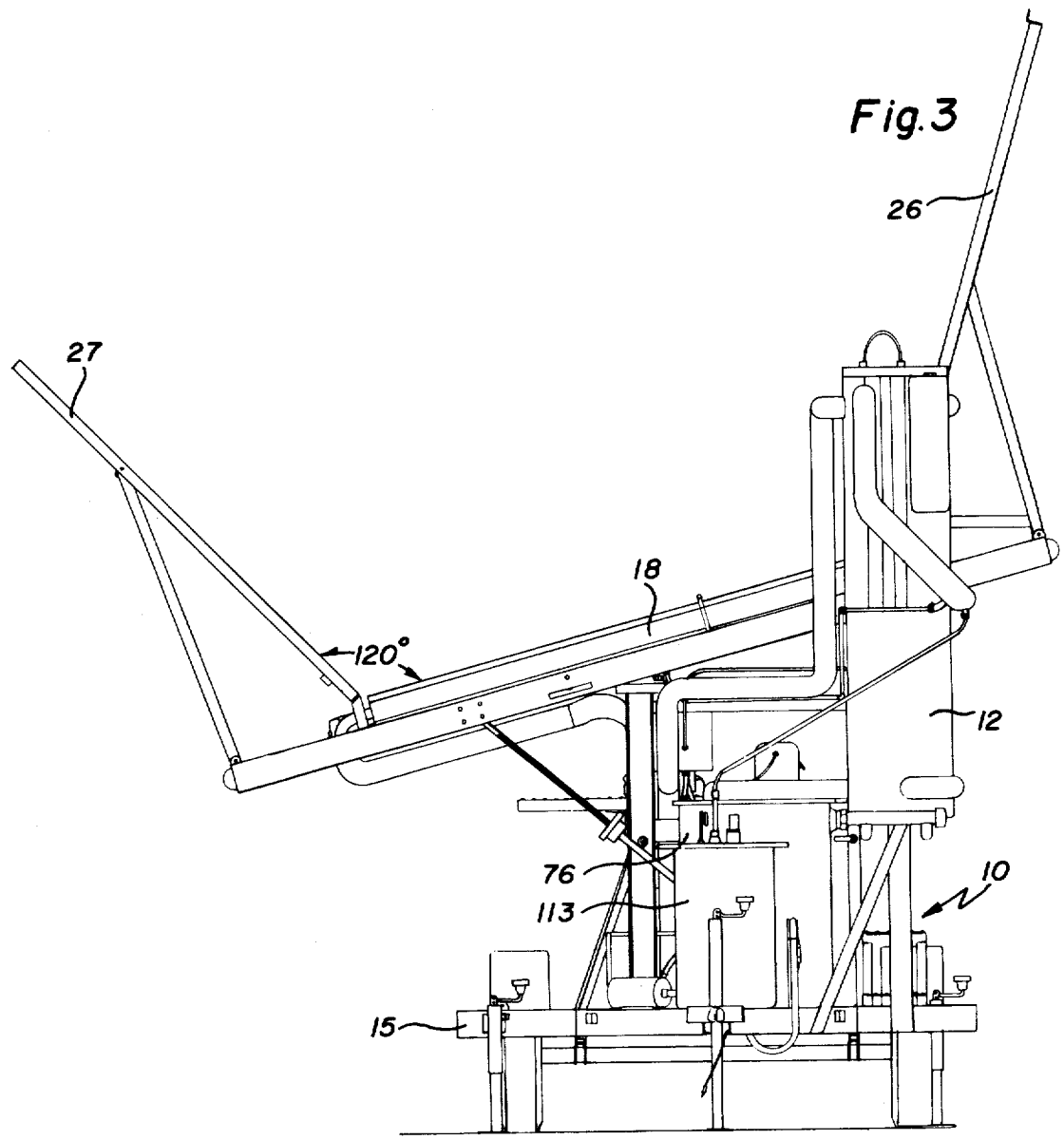

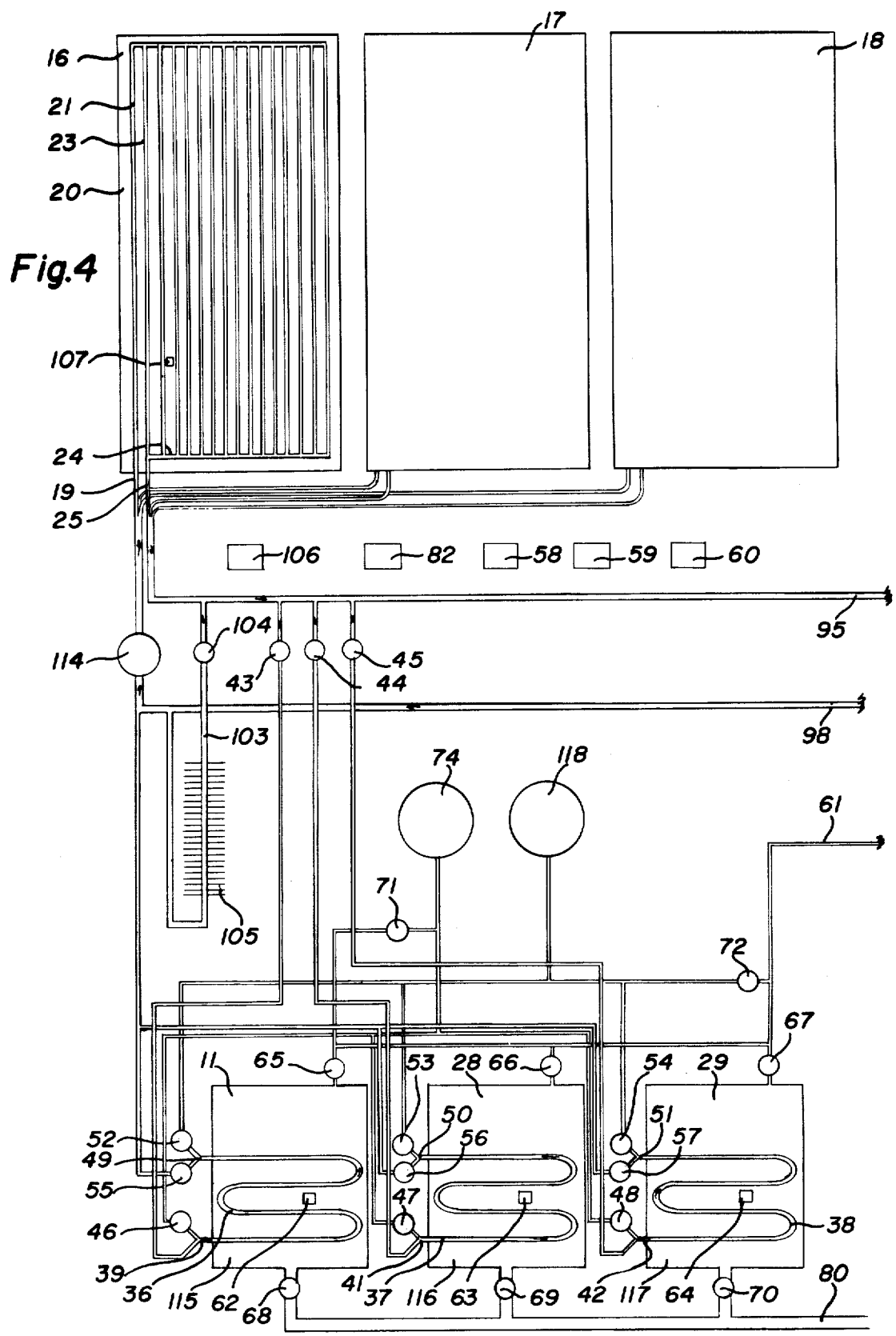

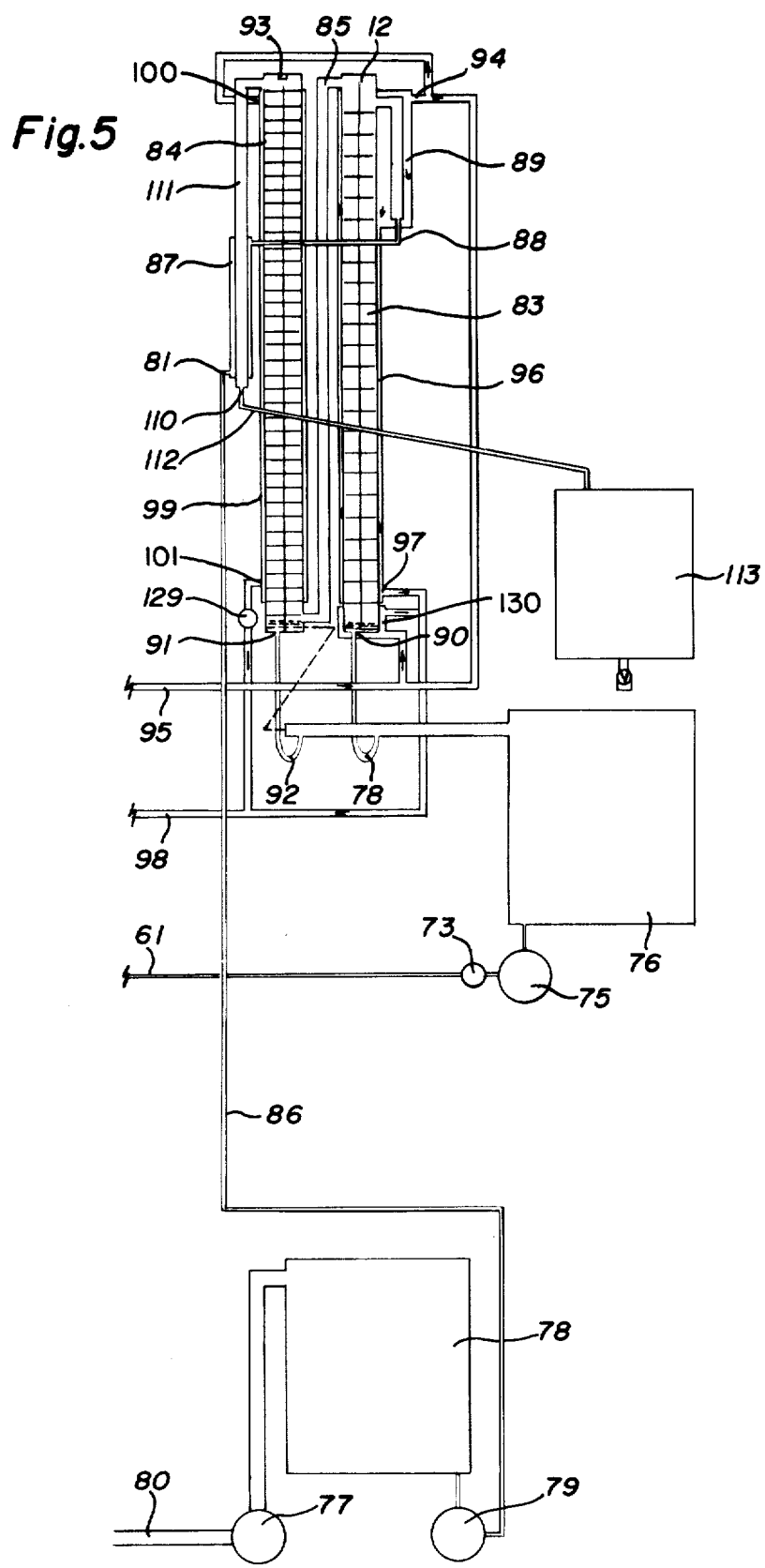

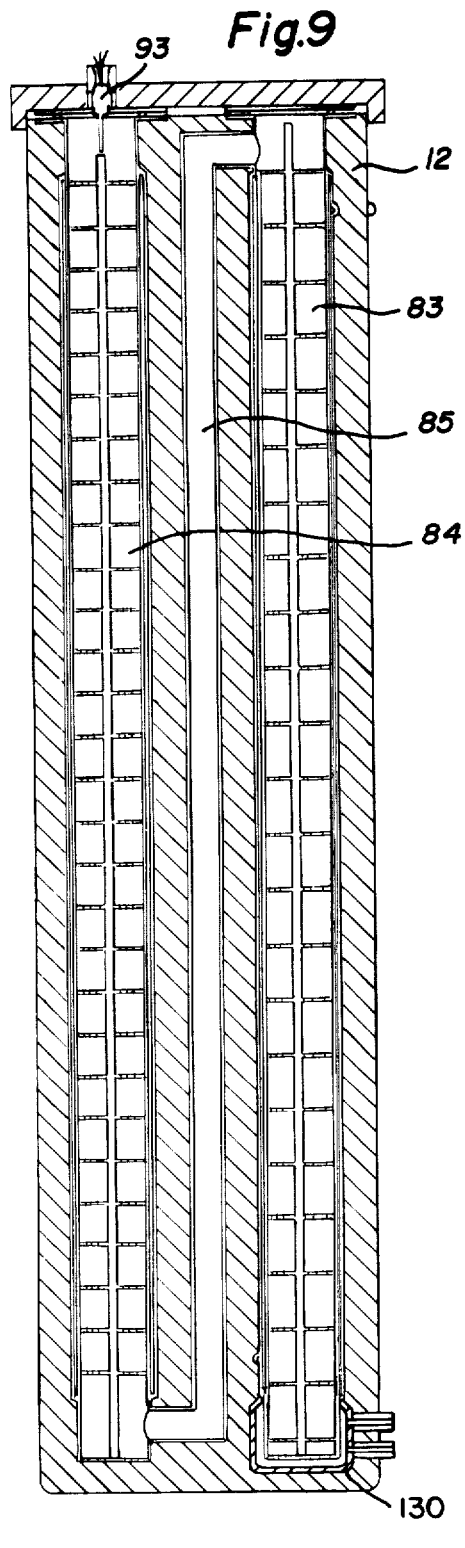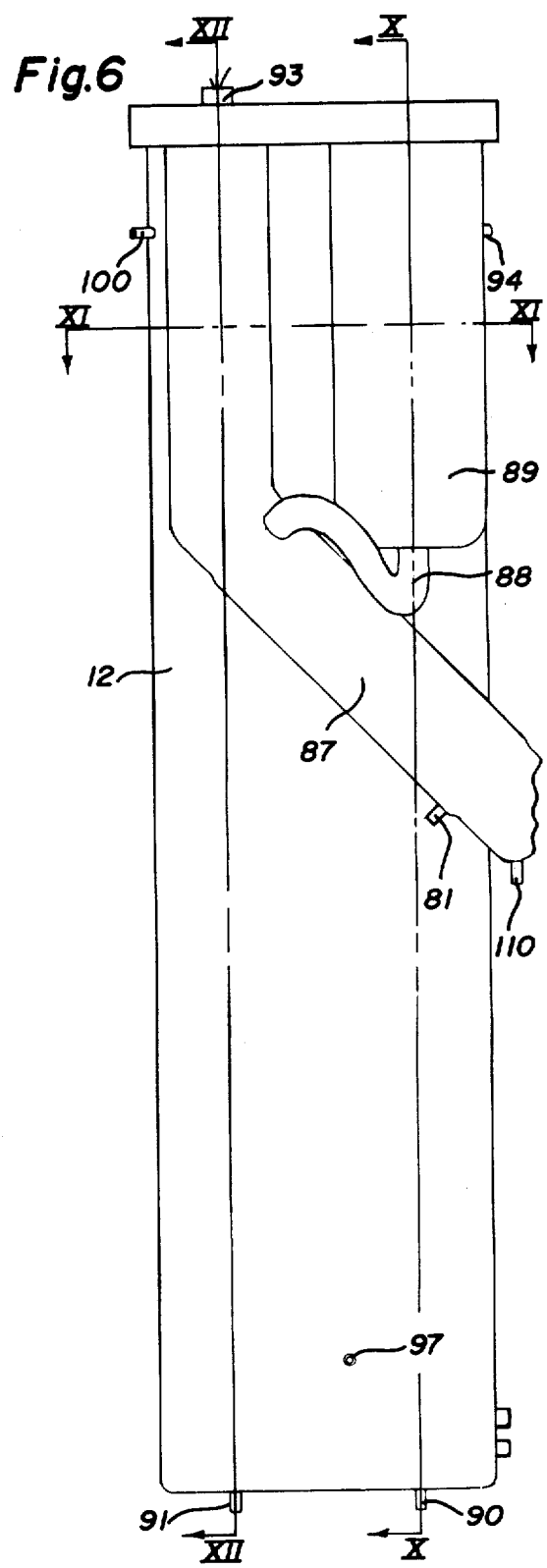

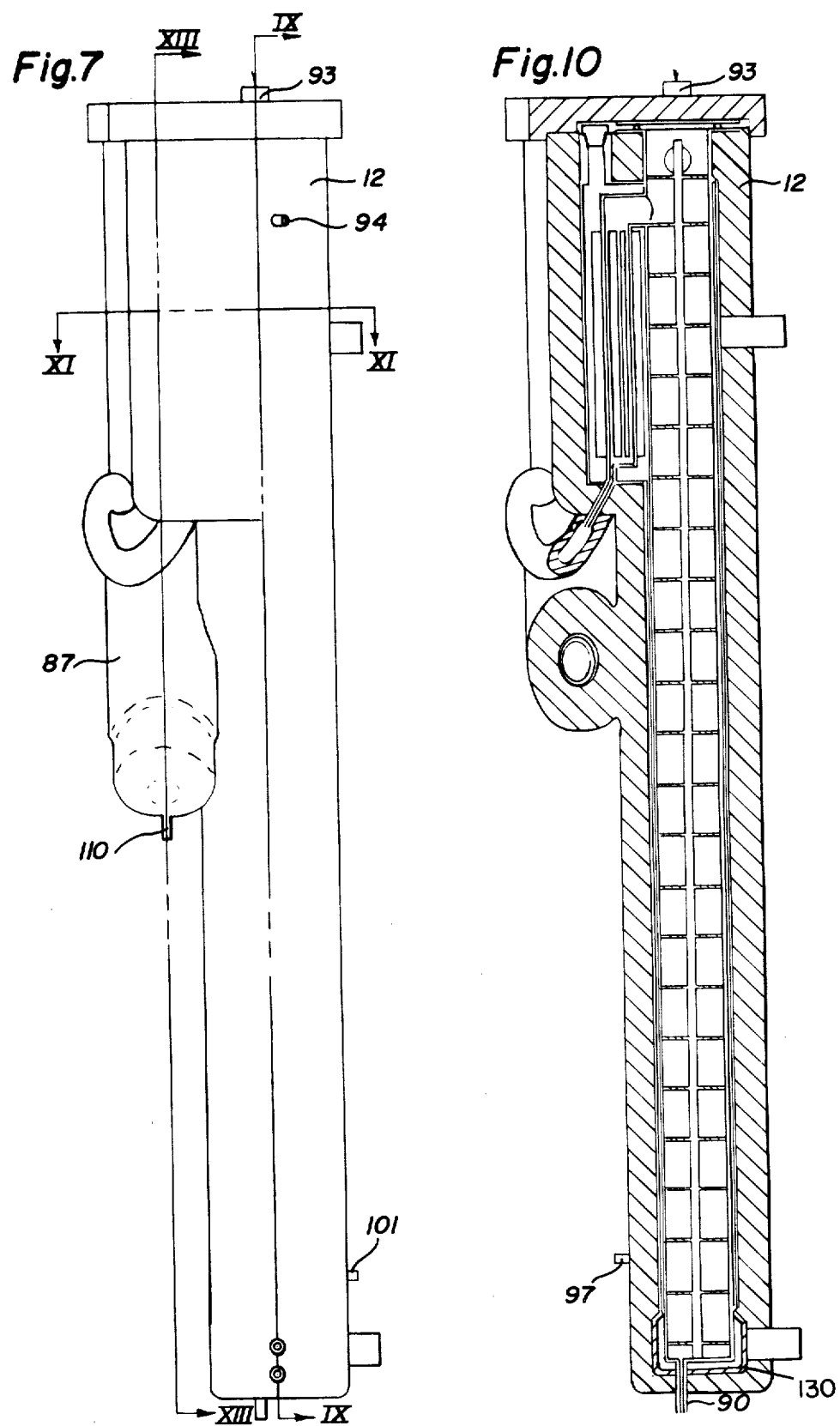

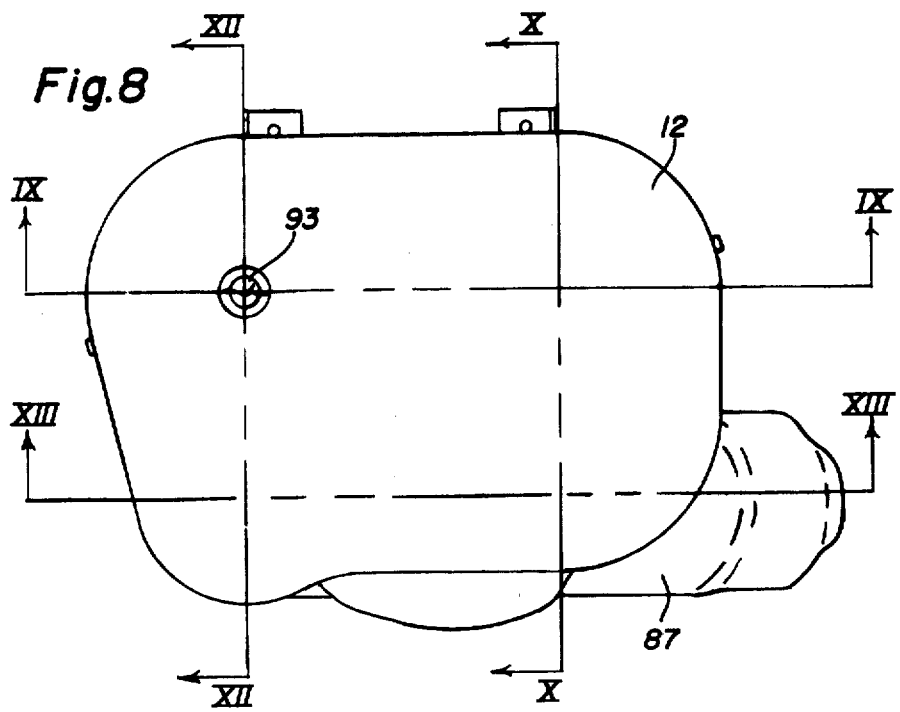
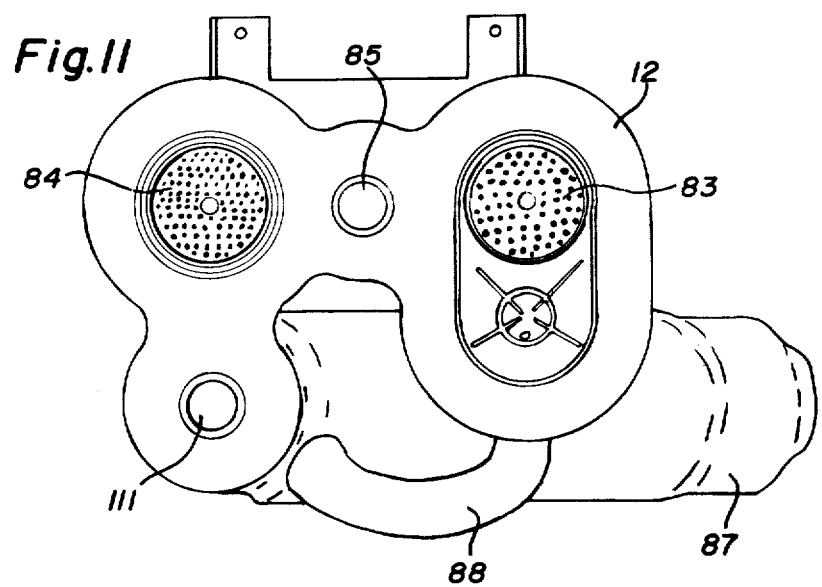

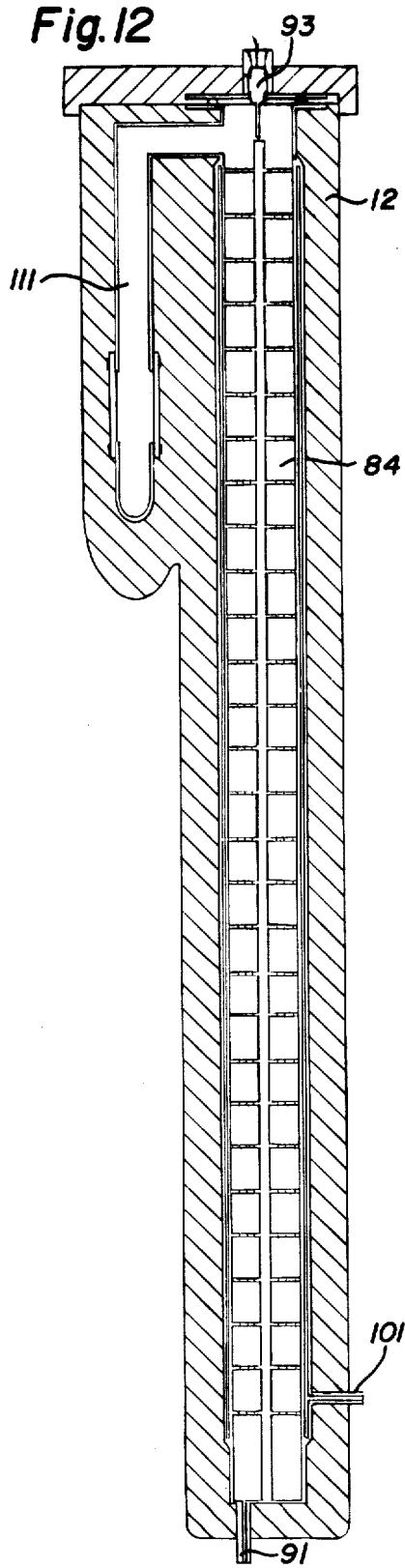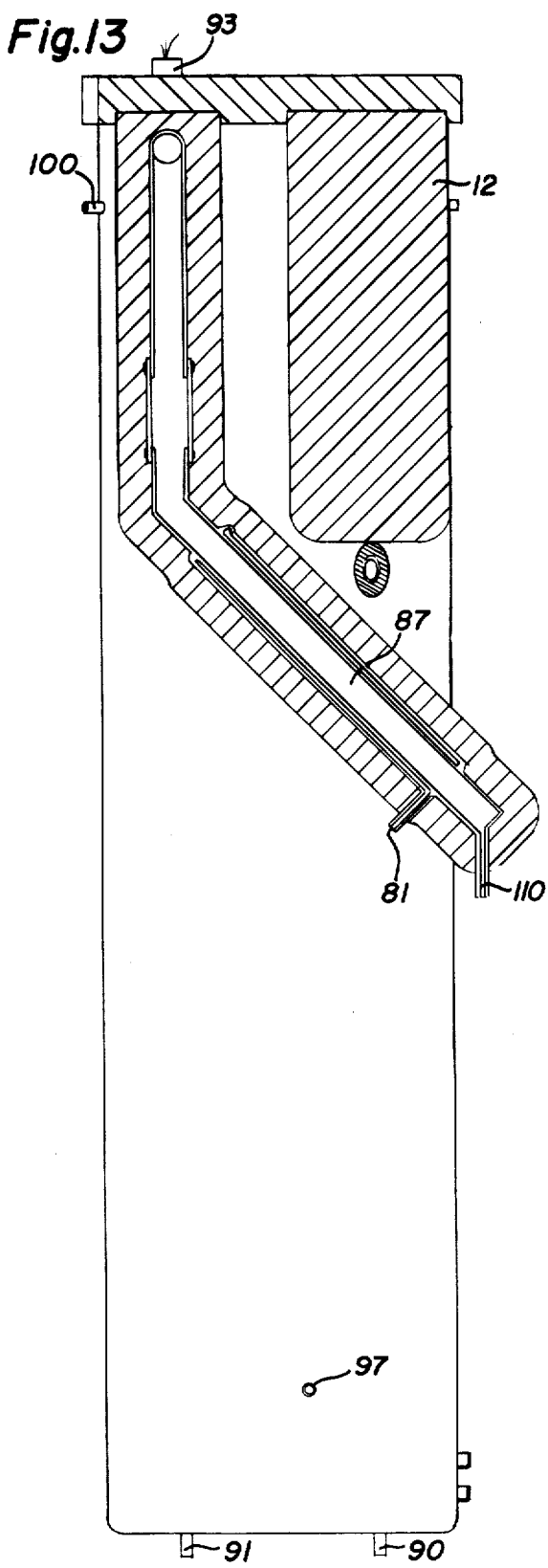

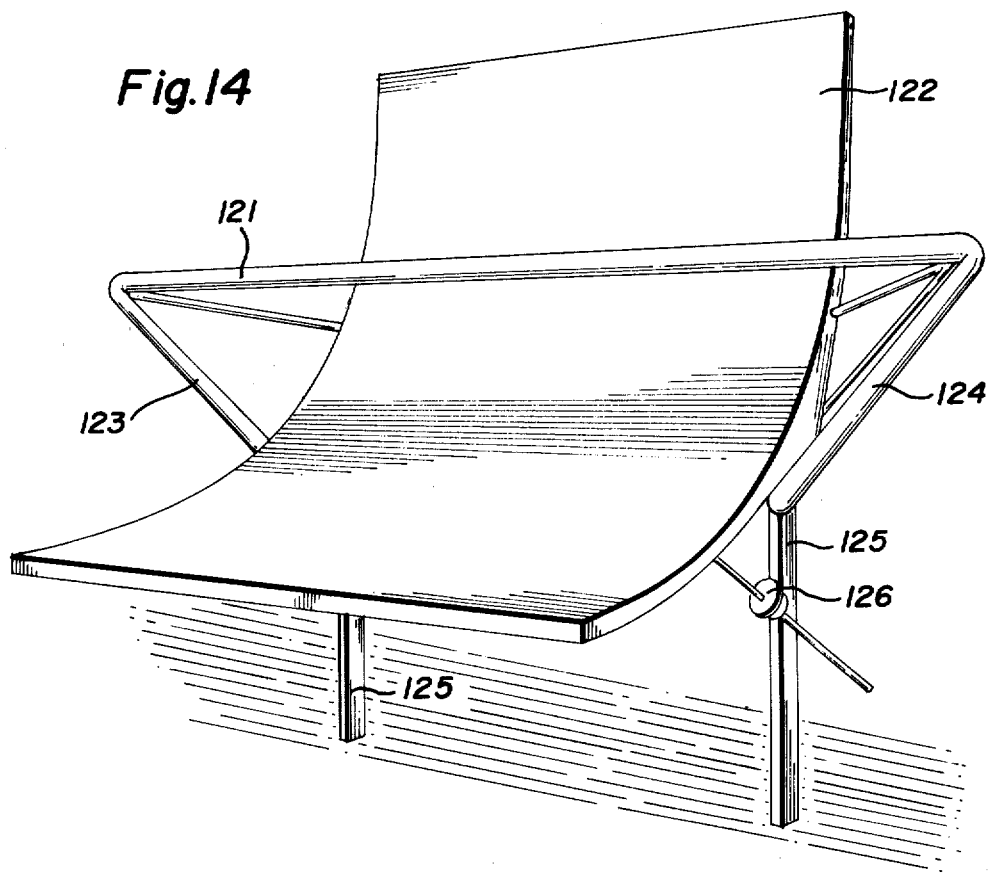

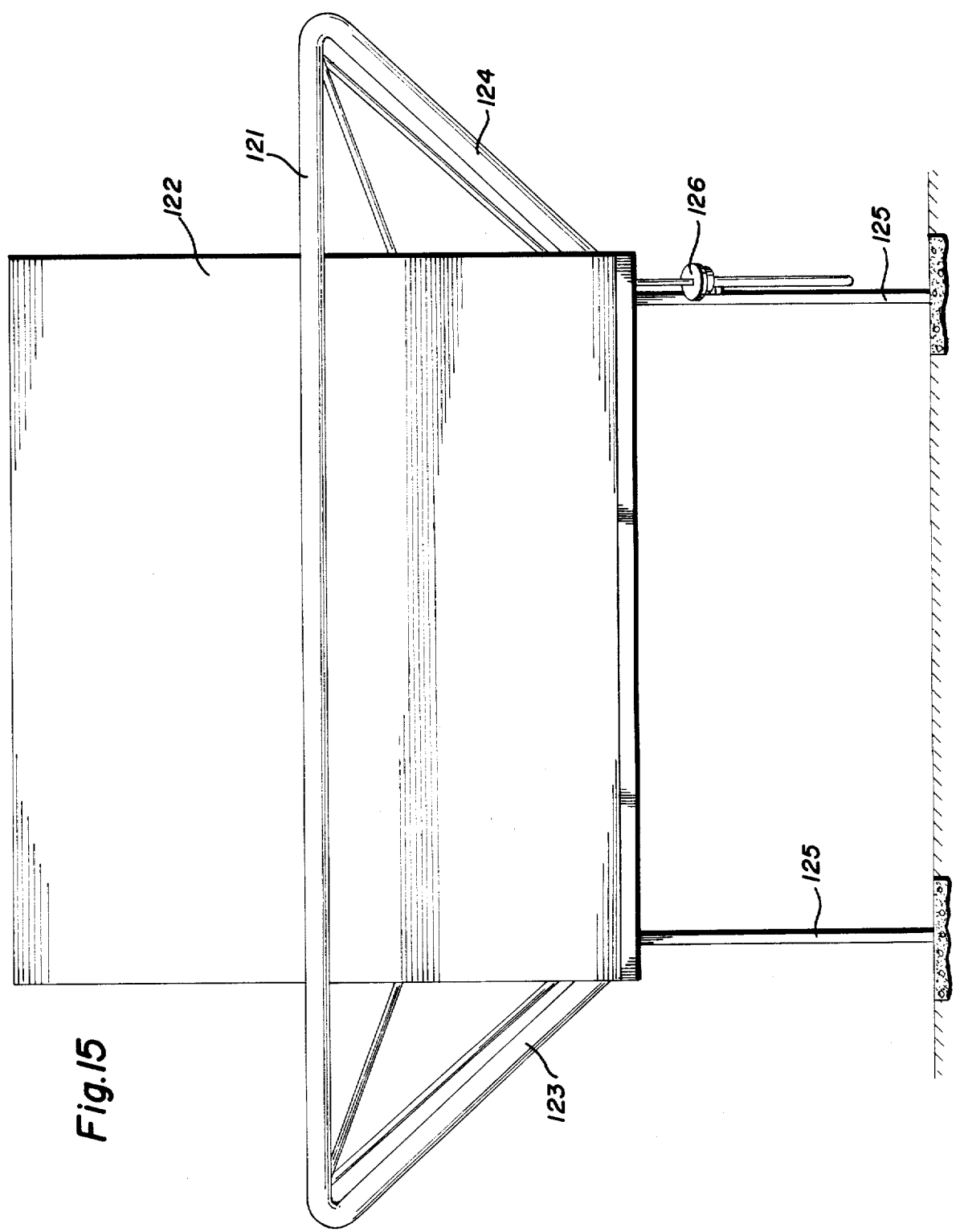

SOLAR STILL

BACKGROUND OF THE INVENTION

Although mankind has always been interested in the use of alcohol as a fuel, up until recent times the cost has always made it prohibitive for most uses. Fuels, such as gasoline and kerosene, that are available from petroleum sources have always been cheaper. Recently, however, the cost of petroleum products has increased considerably and alcohol has become a more interesting material to use as fuel for automobiles or other combustion purposes. One particularly interesting use of alcohol is in the so-called "gasohol" in which about 10% of alcohol is added regular or low-lead gasoline. The alcohol can be added to the gasoline without any special industrial equipment, so that the suggestion has been made that an individual can make his own alcohol in his home and add it to his gasoline to increase his mileage and reduce his monitoring costs. First of all, the average home generates materials that can be used to make alcohol in small amounts. Secondly, the distillation process is a simple one that can be carried out without the use of industrial equipment. It has even been suggested that the heat to carry out distillation processes can be obtained by the sun in a solar still. Attempts, however, in the past to obtain a simple still that can be used in the home has been less then successful, since they have suffered from a number of disabilities. Among other things, they have been intricate and expensive and have required considerable amounts of maintenance to keep them in operating condition. Generally speaking, they do not lend themselves to operations by persons of only ordinary intelligence. These and other difficulties experienced with the prior art devices have been obviated in a novel manner by the present invention.

It is, therefore, an outstanding object of the invention to provide a solar still particularly adapted for home use in the generation of alcohol.

Another object of this invention is the provision of an apparatus for the separation of alcohol from alcohol-containing liquids, which apparatus is capable of use with crude mashes.

A further object of the present invention is the provision of a solar still for use with mashes from farm products or home refuse and garbage.

It is another object of the instant invention to provide a solar still which does not easily become clogged and does not require frequent cleaning.

A still further object of the invention is the provision of a solar still which is simple in construction, which can be made inexpensively from commonly-available materials, and which is capable of a long life of useful service with a minimum of maintenance.

It is a further object of the invention to provide a solar still which can be conveniently used in the home for the generation of alcohols from home wastes.

With these and other objects in view, as will be apparent to those skilled in the art, the invention resides in the combination of parts set forth in the specification and covered by the claims appended hereto.

SUMMARY OF THE INVENTION

In general, this invention is a solar still adapted for the production of fuel-grade ethanol by enzymatic conversion of starch or cellulose into fermentable sugars and subsequent fermentation of the sugars into alcohol. The system can also be used for direct fermentation of agricultural sugars into alcohol. The beer produced by the fermentation is distilled in a continuous fractionating column to the proof desired. All of the heat requirements are provided by solar energy.

The system is comprised of three major components and interfacing controls. One or more fermentation tanks are provided as vessels in which the chemical conversion of the starch materials to a low-alcohol-concentration beer takes place. A distillation unit is provided to separate the beer into a high-alcohol-concentration stream and a very-low-alcohol-concentration stream. A solar collector provides heat to the fermenting tanks and to the distillation unit. Temperature controllers regulate the temperature of the solar collector, the temperature of the high alcohol concentration stream, and the temperatures of the fermentation tanks.

The solar collector is provided with reflective surfaces which increase the effective area of the solar collectors. The reflectors may be in the form of over and under panels or a parabolic cylinder.

BRIEF DESCRIPTION OF THE DRAWINGS

The character of the invention, however, may be best understood by reference to one of its structural forms, as illustrated by the accompanying drawings, in which:

FIG. 2 is a rear elevational view of the solar still shown in FIG. 1, FIG. 3 is a side elevational view of the solar still shown in FIG. 1, FIGS. 4 and 5 taken together represent a schematic representation of the interconnections between the various major elements of the solar still shown in FIG. 1, FIG. 6 is a front elevational view of a fractionating column particularly adapted for practicing the present invention, FIG. 7 is a side elevational view of a fractionating column shown in FIG. 6, FIG. 8 is a plan view of the fractionating column shown in FIG. 6, FIG. 9 is a front elevational sectional view of the fractionating column taken on the line IX—IX of FIG. 7, FIG. 10 is a side elevational sectional view of the fractionating column taken on the line X—X of FIG. 6, FIG. 11 is a plan sectional view of the fractionating column taken along the line XI—XI of FIG. 6, FIG. 12 is a side elevational sectional view of the fractionating column taken along the line XII—XII of FIG. 6, FIG. 13 is a front elevational sectional view of the fractionating column taken on the line XIII—XIII of FIG. 7, FIG. 14 is a perspective view showing an alternative solar collector set-up useful in practicing the present invention, FIG. 15 is a front elevational view of the solar collector shown in FIG. 14.

DESCRIPTION OF THE PREFERRED EMBODIMENT

Figure 1:
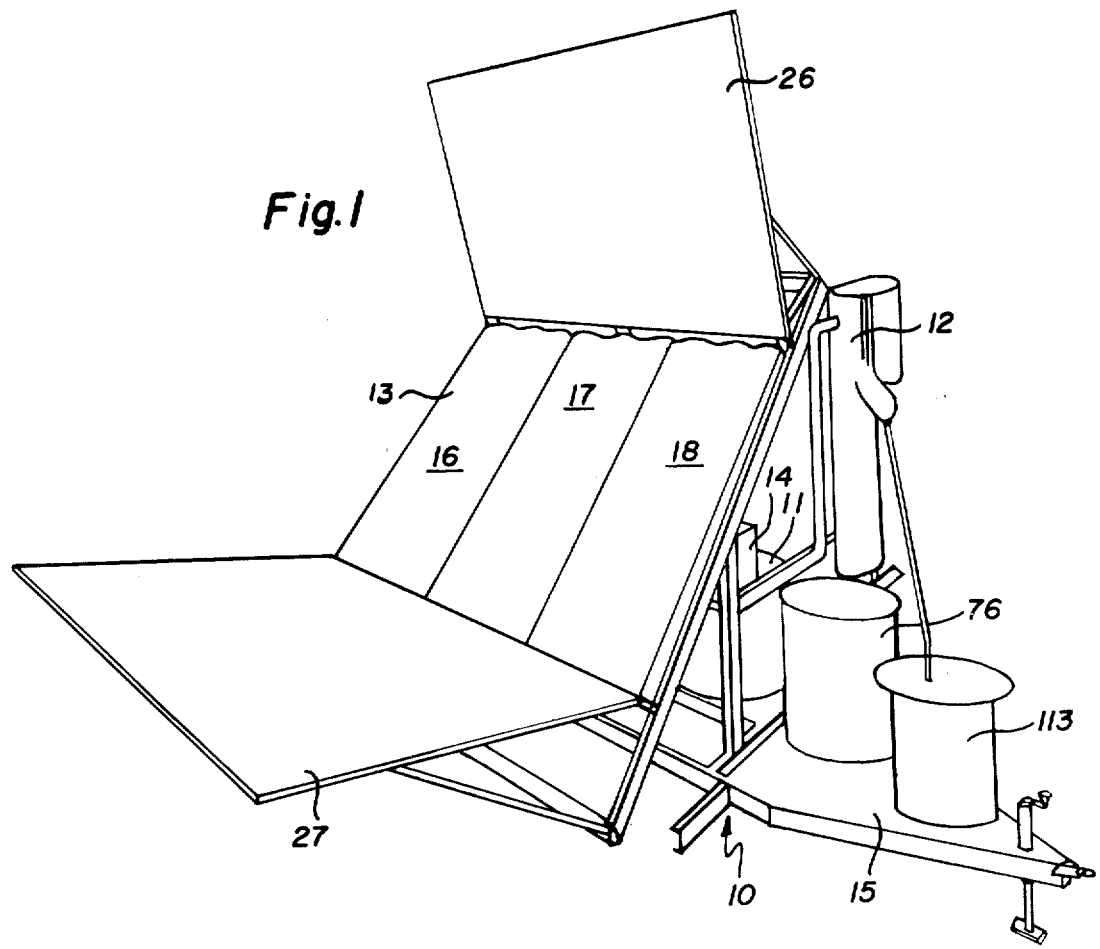
FIG. 1 is a perspective view of a solar still incorporating the principles of the present invention.

Referring first to FIG. 1, wherein are best shown the general features of the invention, the solar still, indicated generally by the reference numeral 10, is shown as having a fermenting tank 11, a distillation unit 12, a solar collector 13, and a control center 14. In the embodiment shown in FIG. 1, the entire unit is mounted on a single, car-towable trailer 15.

The solar collector 13 shown in FIG. 1, includes three solar collector panels 16, 17 and 18 of generally conventional design. The main body of each panel consists of a copper plate across which fluid flow conduits are formed. Referring to FIG. 4, it can be seen that solar panels 16 has a working fluid inlet port 19 at its lower edge. The inlet port 19 provides fluid to a riser 21 which in turn provides fluid to an upper manifold 22. From the upper manifold 22 descend a large number of downcomers 23 which carry fluid to the lower manifold 24, and thence to the outlet port 25. The sun-facing side of the plate 20 has a sheet of clear plastic glazing placed over it. This sheet cuts down heat loss due to conduction and convection. The sunny side of the plate is also coated with a paint formed of finely divided cupric oxide in a clear acrylic carrier. It was found that the surface of a copper plate which was chemically converted to cupric oxide had the property that the surface became an extremely effective absorber of solar radiation, but a very poor radiator of heat energy in the temperature ranges normally encountered in the present solar panels. Surprisingly, this same desirable effect has been found to occur when the cupric oxide is applied to the surface in the form of a paint formulated with about 25 wt percent of the cupric oxide.

Referring back to FIG. 1, it can be seen that the solar panels have planar reflective panels 26 and 27, mounted on their upper and lower edges. The panels are mounted so that each reflective panel forms an angle of 120° with the solar panel. In this way, the effective surface area of the solar panel is substantially increased because light which strikes the reflective panels is reflected onto the solar panels. An important result of the over and under reflector panels is that the collector can be aimed at the expected noon-time position of the sun and will efficiently absorb solar radiation all day without the need for further adjustment or tracking.

Referring now to FIG. 2, it can be seen that the preferred embodiment is provided with three fermentation tanks 11, 28, and 29. It has been found that, with proper processing, a tank of raw mash can be ready for distillation in three days. Thus, by using three tanks and loading one each day, a tank can be ready for distillation each day.

Each tank is a 70 gallon insulated plastic container provided with a liquid level sight 31, 32 and 33, an electric pH meter 34 (not shown), and a pulper-stirrer 35. The pulper-stirrer 35 is provided in the system and is adapted so that it can be used on each of the fermenting tanks. The pulper-stirrer 35 is a 1 h.p., 2-speed, vertical-shaft device with a mounting bracket and splash guide that positions the motor at the top center of the fermenting tank being processed. The motor drives a pair of radially-canted blades. Slow speed is for stirring.

The schematic view of the fermenting tanks 11, 28 and 29 in FIG. 4 shows other equipment used in the tanks. Each tank is provided with a heating-cooling coil 36, 37 and 38. The input ends 39, 41 and 42 of heating-/cooling units 36, 37 and 38 are connected to heated fluid valves 43, 44, 45, respectively, and cooling water supply to valves 46, 47 and 48, respectively. The output ends 49, 50 and 51 of coils 36, 37 and 38 therefore, respectively, are connected to drain valves 52, 53 and 54, respectively, (which are connected to a disposal drain 118), and working fluid return valves 55, 56 and 57, respectively. The valves associated with fermentation tank 11, namely, valves 43, 46, 55, and 52, operate under the control of temperature controller 58. The valves associated with fermentation tank 28, namely, valves 44, 47, 56, and 53, operate under the control of temperature controller 59. The valves associated with fermentation tank 29, namely, valves 45, 48, 57, and 54, operate under the control of temperature controller 60. Each temperature controller 58, 59, and 60, is associated with a temperature sensor 62, 63, and 64 in fermentation tanks 11, 28, and 29, respectively. Thus, the temperature controllers 58, 59, and 60 are able to maintain the temperature within the fermentation tank within a preselected temperature range.

The fermentation tanks are each provided with a liquid fill port 65, 66, and 67, on the top. The top of each tank are removable for ease in loading and unloading the mash. Each tank is also provided with a liquid drain port 68, 69 and 70, at the bottom.

The fill ports 65, 66 and 67 are connected to a piping and valve system, including valves 71, 72 and 73 to allow the fill port to be selectively connected to the water supply 74 or, through tubing 61 and pump 75, to the water-receiving tank 76 which holds the water-rich product of the distillation unit 12. The drain ports 68, 69 and 70 are connected by tubing 80, through pump 77, to the beer holding tank 78. The beer holding tank 78 is in turn connected through tubing, and through pump 79 to the beer input port 81 of the distillation unit 12. The pump 79 is connected to distillation unit temperature controller 82.

The bottoms of mashing tanks 11, 28 and 51 are covered with screens 115, 116 and 117, respectively, which keep the mash from draining through the drain valve 68, 69 and 70, respectively, when the liquid in the tanks is being drained.

Referring to FIGS. 5-13, the distillation unit 12, in the preferred embodiment, is a 42-plate, aluminum, continuous-distillation column having a separate stripping section 83 and rectification section 84, arranged in a side-by-side geometry. The two sections are connected by a central top-to-bottom transfer conduit 85. The beer input port 81 of the distillation unit 12 is supplied with beer from a 70 gallon, insulated, plastic, beer-holding tank 78, through explosion-proof pump 79 and conduit 86. From the beer input port 81, the beer flows through a heat-exchanger 87, counter-currently with the alcohol-rich product. From the heat-exchanger 87, the beer flows through conduit 88 to heat-exchanger 89, where it flows counter-currently with the working fluid from the solar collector. The beer then enters the upper end of the stripping section 83. The vapors pass through the transfer conduit 85 to the rectification section 84, while the liquid passes downward through the stripping section 83. The bottom fraction of the stripping section 83 is essentially water and passes out a first water exit port 90 through a trap 78 and onto a 70 gallon insulated-plastic water receiver 76.

The bottom fraction of the rectification section 84, which contains water and a very small amount of alcohol, passes out a second water exit port 91, through trap 92, and into the receiving tank 76. Both traps 78 and 92 are on level with the still pots (shown by dashed line) to maintain liquid at the bottom of each section 83 and 84.

The vapor phase continuously moves up the stripping section 83, down the transfer conduit 85, and up the rectification section 84, becoming increasingly rich in alcohol, until it reaches the alcohol-water azeotrope (95% alcohol). As it passes out the top of the rectification section 84 its temperature is measured by temperature sensor 93. The alcohol-rich vapor then passes down conduit 111, through heat-exchanger 87, out exit port 110, along conduit 112, to a 30-gallon, uninsulated-plastic, alcohol receiver 113.

Temperature sensor 93 communicates the temperature of the alcohol-rich stream to the column temperature controller 82. The controller 82 maintains the alcohol-rich stream temperature at approximately 173° F. by regulating the beer input flow caused by pump 79. The heated working fluid which provides the energy for distillation, arrives at the working fluid input port 94 through conduit 95. The working fluid then passes through heat-exchanger 89, where it heats up the incoming beer, and then into a heating jacket 96, around the stripping section 83. The working fluid then passes out exit port 97 and through conduit 98, and back to the solar collector, through pump 114. Pump 114 is connected to solar panel temperature controller 106 and causes the working fluid to circulate when the panels are at a temperature of 212° F. or greater. All temperatures are expressed in degrees F. Conduit 95 also provides heated working fluid to a water jacket 99 around the rectification section 84 by passing fluid into an input port 100 and out an exit port 101. A valve 129 stops the flow of working fluid when controller 93 indicates that the alcohol temperature is 173° or above. This minimizes the inefficiency of still start-up. Conduit 95 also supplies heated working fluid to still-pot heating jacket 130.

Between the working fluid conduits 95 and 98 is a thermal dump leg 103 which includes a valve 104 and a radiator 105. The valve 104 is controlled by solar panel temperature controller 106. The solar panel temperature controller 106 reacts to a temperature sensor 107 in one of the solar panels. By dissipating heat through the radiator, valve 104 is able to maintain the temperature of the solar panel below 225° F.

Figure 16:
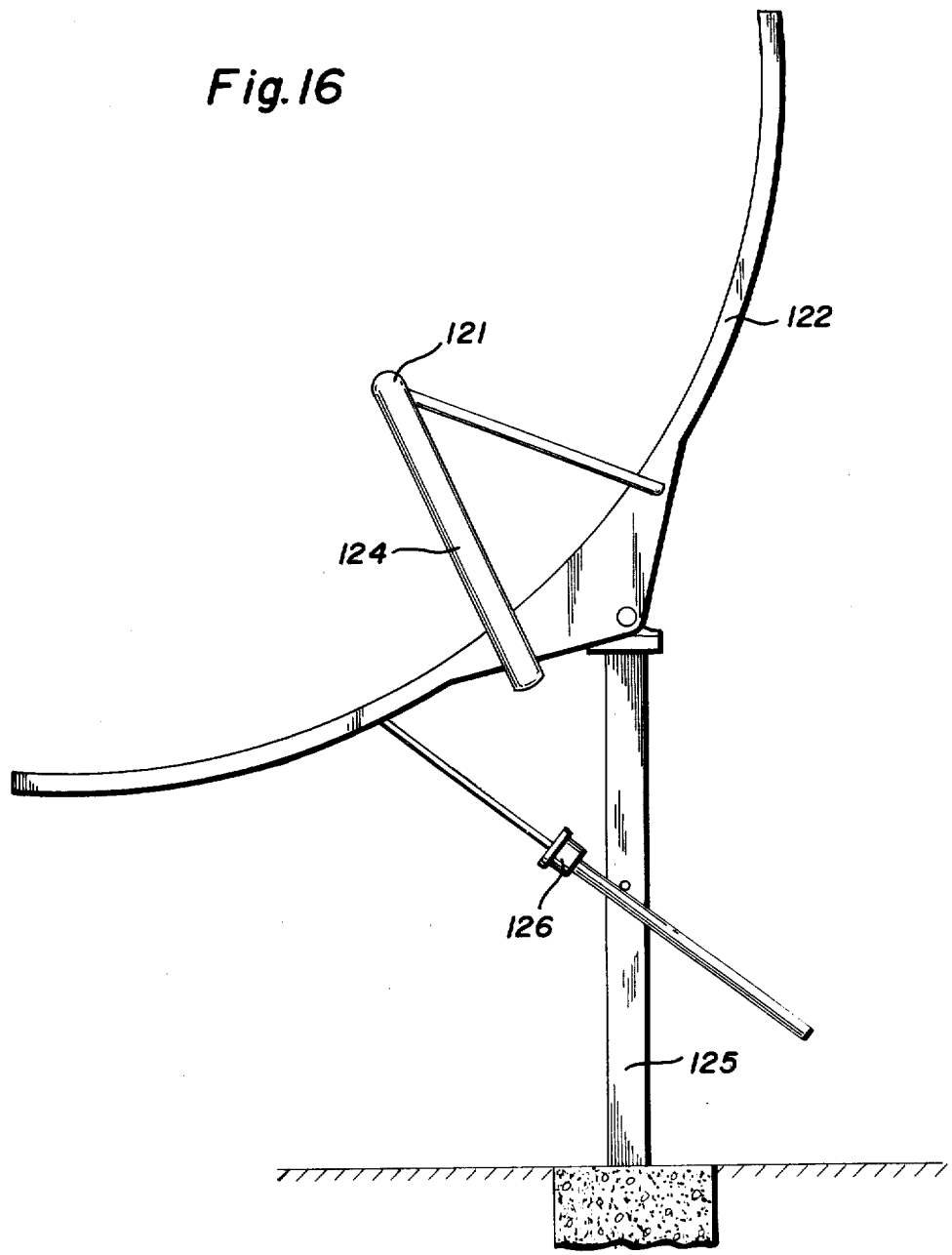
FIG. 16 is a side elevational view of the solar collector shown in FIG. 14.

An alternative version of the solar collector 13 is shown in FIGS. 14, 15, and 16. In the alternative version, the solar panels 16, 17 and 18 are replaced by a radiation-absorbing pipe 121 through which the working fluid flows. The radiation-absorbing pipe 121 is positioned at the focal line of a parabolic reflector 122. The parabolic reflector is in the form of a cylinder having a parabolic directrix, and having the concave surface rendered reflective. The pipe 121 extends along the focal line of the reflector and a substantial distance beyond each of the axial ends of the reflector. In this way, the radiation-absorbing pipe 121 remains in the path of light reflected from the reflector 122 even though the sun is not directly in front of the reflector. The pipe 121 is connected through conduits 123 and 124 to inlet and outlet ports analagous to inlet port 19 and outlet port 25 in the construction shown in FIGS. 4 and 5. Thus, the working fluid is circulated through conduit 124, pipe 121, conduit 123, and thereby heated, and thereby functions in the same manner as described in the earlier embodiment.

The pipe 121 and reflector 122 are mounted together for movement about a horizontal axis on base 125. Locking means 126 is provided to hold the reflector in a chosen position.

The pipe 121 and reflector 122 may be enclosed in a transparent envelope to reduce heat loss. The envelope may be evacuated in order to further decrease heat loss.

In operation, the parabolic solar collector is positioned so that a line through the focus and vertex of a directrix of the reflector intercepts the arc that sun makes in its daily migration across the sky. This adjustment must be made each day, but need only be made once each day because the geometry of the pipe 121, as it extends beyond the edges of the reflector, allows the solar collector to be effective during the entire daily path of the sun across the sky. Thus, there is no need for constant tracking of the sun by the collector.

OPERATION: CORN TO ALCOHOL

Preliminaries

1. The solar collector B is positioned so that its axis is in the east-west direction and level.
2. Place power switch in "off" position. The electric cord is plugged into a standard 110 volt, 60 cycle, 15 amp receptacle.
3. The cooling water line is hitched by a standard garden hose to a cold water faucet.
4. The drain line is run by a garden hose to a water drain.

Day 1

1. Make sure all drain gates and manual water valves are closed. 2. Set controls
   (a) solar panel temperature controller 106 at 212°
   (b) distilling temperature controller 82 at 195°
   (c) fermenting tank 11 controller 58 heat to 220°
   (d) fermenting tank 28 controller 59 heat to 40°
   (e) fermenting tank 29 controller 60 heat to 40°
   (f) fluid transfer to or from fermenting tank is off
   (g) power on
3. Adjust solar collector so that a line perpendicular to the plane of the absorber panel 18 and passing through the area of the absorber panels subtends the arc. The sun makes in its migration across the sky on the day of adjustment.
4. The pulper-stirrer is placed in fermentation tank 11.
5. Two bushels (112 lbs.) of whole kernel or cracked corn is placed in the tank 11. Then turn to stir.
6. Water is added to mash level on sight glass 31.
7. pH measurement is taken with the pH meter 34 and adjusted to 6.0-6.5.
8. Add 2 oz. alpha-amalase enzyme.
9. When temperature has risen to 140° turn on pulper 35 for 15 minutes.
10. When temperature reaches 205°, let set for ½ hour.
11. Set temperature control to 135°, add water to ferment level on sight glass 31, if mash temperature still above 140°, operate coil 36 to cool mash.
12. Turn on stirrer 35. Set pH to 3.5-4.5.
13. When temperature reaches 136°-140° add 3 oz. gluco amalase enzyme. Stir 2 hours.
14. Turn control to 85° and set to cool. Stir to promote cooling. When temperature has reached 90° add 5 oz. active yeast, stir in for 5 minutes.
15. Remove stirrer 35 and place it in mash tank 28.
16. Clamp cover on mash tank 11.

Day 2

1. Set controls
   (a) solar panel temperature controller 106 at 212°
   (b) distilling temperature controller 82 at 220°

(c) fermentation 11 controller 58—cool to 85°
(d) fermentation tank 28 controller 59 heat to 212°
(e) fermentation tank 29 controler 60 heat to 40°

2. Follow steps 3-14 from day 1 but apply them to tank 28.

3. Remove stirrer-pulper 35 and place it in mash tank 29.

4. Clamp cover on mash tank 28.

Day 3

1. Set controls
(a) solar panel temperature controller 106 at 212°
(b) distilling temperature controller 82 at 220°
(c) fermentation tank 11 controller 58 cool to 85°
(d) fermentation tank 28 controller 59 cool to 85°
(e) fermentation tank 29 controller 60 heat to 212°

2. Follow steps 3-14 from day 1, but apply them to tank 28. 3. Remove stirrer-pulper from tank 29 and place it on rack.

4. Clamp cover on mash tank 29.

Day 4

1. Set collector angle as in step 3 of day 1.
2. Open gate valve 68 on tank 11.
3. Turn on fluid transfer pump 77 until mash tank 11 is drained.
4. Shut gate valve 68.
5. Set distilling temperature controller 82 to 173°.
6. Remove cover from tank 11 and place in stirrer 35.
7. Add water to mash level on sight glass 31.
8. Turn on stirrer for 5 minutes.
9. Open gate 68.
10. Turn on pump 77 to drain tank.
11. Shut gate 68.
12. Scoop out residue (distillers feed) from tank 11.
13. Follow steps 4-16 from day 1.
14. Pump 79 is turned on to pump beer into the distillation unit under the control of controller 82 and sensor 93.
15. The distillation operation creates an alcohol-rich product which collects in receiver 113, and an alcohol-weak product which collects in receiver 76, and is recirculated to the fermenting tanks to conserve alcohol and heat. The two bushels of corn produce 6 gallons of 190 proof alcohol.

Day 5

Follow procedure for Day 4, but apply it to tank 28.

OPERATION: NEWSPAPER TO ALCOHOL

This operation is the same as that for corn except for the following variations.

1. 40 gallons of water are put into the fermenting tank.

2. 0.64 of dray trichoderma viride cellulase is mixed with a cup of warm (100° F.) water until it becomes suspended. This is added to the mashing tank. If the cellulase is added directly to the fermenting tank, it will float on top of the water and stick to the sides of the tank.

3. The tank is heated to 120° F.

4. The pulper is turned on.

5. 50 lbs. of newspaper is added to the tank, a little at a time, so that an emulsion is formed.

6. When the paper is pulped (about 10 minutes), the pulper is turned to stir and the enzymatic conversion is allowed to proceed for 24 hours.

7. After 24 hours the solution is cooled to 85° and two ounces of yeast is added.

8. Fermentation is allowed to proceed to completion (48 hours).

9. The liquid (beer) is removed by suction to the distillation holding tank.

10. The beer is distilled in the usual way. Yield is 2.7 gallons of 190 proof alcohol.

It can be seen, then, that the present invention provides a very simple solar still that makes use of the energy of the sun to obtain small quantities of alcohol commensurate with the operation of a motor vehicle or the like. It can be used in a non-industrial atmosphere to make use of suitable residential or foam by-products, garbage and the like. It is easy to keep the apparatus clean and it is so simple that very little maintenance is required to keep it operative. It is rugged in construction and not capable of being rendered ineffective by the weather and by careless usage.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A solar still for producing alcohol, comprised of:
(a) at least one fermenting tank adapted to produce a beer by fermentation,
(b) a heat exchanger,
(c) a solar collector adapted to absorb energy from the sun and use that energy to heat a working fluid,
(d) a working fluid conveying system adapted to circulate the working fluid through the solar collector and through the heat exchanger,
(e) a distillation unit comprising:
(1) a stripping fractioning column,
(2) a rectification fractioning column, and
(3) a transfer conduit operatively connecting the top of the stripping column to the bottom of the rectification column,
(f) transferring means adapted to convey the beer from the fermenting tank to the heat exchanger, wherein energy from the working fluid is transferred to the beer, the beer and the working fluid flowing in separate conduits so that the beer and working fluid never mix, and
(g) means for conveying the beer from the heat exchanger to the top of the stripping column where the beer is divided into an alcohol rich vapor phase stream which passes through the transfer conduit to the rectification column where it moves up the rectification column and an alcohol weak stream which flows downwardly through the stripping column, whereby beer in the vapor phase from the alcohol weak stream moves up the stripping column, through the transfer conduit to the bottom of the rectification column and up the rectification column.

2. A still as recited in claim 1, wherein at least three fermenting tanks are provided.

3. A still as recited in claim 1, wherein means are provided for conveying the alcohol rich stream from the top of the recitification column and a heat recovery device is provided to transfer heat from the alcohol rich stream leaving the rectification column, to the beer entering the stripping column.

4. A still as recited in claim 1, wherein the solar collector includes a planar absorber having conduits through which the working fluid flows, the absorber having an upper edge, a lower edge, and a sunny side, wherein a reflective panel is attached to at least one of either the upper or lower edge and angled with respect to the plane of the absorber to cause solar radiation striking the reflective panels to be reflected to the absorber, the intersection of the plane of the reflective panel and of the absorber being substantially horizontal.

5. A still as recited in claim 1, wherein at least a portion of the collector on which the sun shines is covered with a paint comprised of a clear carrier in which has been mixed a dispersion of fine particles of cupric oxide.

6. A still as recited in claim 1, wherein the solar collector is formed of a cylindrical reflector having a parabolic directrix, and an absorbing pipe along the focal line of the reflector, and extending substantially beyond the axial end of the reflector, the reflector being positioned with the focal line horizontal and parallel to the apparent daily path of the sun.

7. A still as recited in claim 1, wherein the working fluid conveying system is adapted to selectively provide heat to the fermenting tank.

8. A still as recited in claim 7, wherein a fermenting tank temperature controller is provided to maintain the temperature within the fermenting tank by regulating the flow of working fluid to the fermenting tank.

9. A still as recited in claim 1, wherein the working fluid conveying system is provided with a thermal dump adapted to selectively exhaust energy from the working fluid.

10. A still as recited in claim 9, wherein a solar collector temperature controller is connected between the solar collector and the thermal dump and adapted to cause the thermal dump to exhaust energy from the working fluid when the temperature of the solar collector reaches a specific value.

11. A still as recited in claim 1, wherein a column controller is provided to regulate the flow of beer into the distillation unit in response to the temperature of the alcohol rich stream.

* * * * *